United States Patent
Gordon et al.

(10) Patent No.: US 9,029,189 B2
(45) Date of Patent: May 12, 2015

(54) BICYCLIC GUANIDINES, METAL COMPLEXES THEREOF AND THEIR USE IN VAPOR DEPOSITION

(75) Inventors: Roy Gerald Gordon, Cambridge, MA (US); Leonard Neil Jacques Rodriguez, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 572 days.

(21) Appl. No.: 12/918,785

(22) PCT Filed: Feb. 20, 2009

(86) PCT No.: PCT/US2009/034708
§ 371 (c)(1), (2), (4) Date: Feb. 24, 2011

(87) PCT Pub. No.: WO2009/105668
PCT Pub. Date: Aug. 27, 2009

(65) Prior Publication Data
US 2011/0151615 A1    Jun. 23, 2011

Related U.S. Application Data

(60) Provisional application No. 61/030,063, filed on Feb. 20, 2008.

(51) Int. Cl.
| | | |
|---|---|---|
| C07D 487/04 | (2006.01) | |
| C07F 15/06 | (2006.01) | |
| C07F 15/04 | (2006.01) | |
| C07F 15/00 | (2006.01) | |
| C07F 7/28 | (2006.01) | |
| C07F 7/00 | (2006.01) | |
| C23C 16/00 | (2006.01) | |
| C23C 16/44 | (2006.01) | |
| H01L 51/40 | (2006.01) | |
| C23C 16/18 | (2006.01) | |

(52) U.S. Cl.
CPC .............. *C23C 16/18* (2013.01); *C07D 487/04* (2013.01); *C07F 7/00* (2013.01); *C07F 15/0053* (2013.01)

(58) Field of Classification Search
None
See application file for complete search history.

(56) References Cited

U.S. PATENT DOCUMENTS

| | | |
|---|---|---|
| 2,613,211 A | 10/1950 | Hurwitz et al. |
| 2,816,896 A | 1/1957 | McKay et al. |
| 4,293,682 A | 10/1981 | Kluger et al. |
| 4,797,487 A | 1/1989 | A'Court |
| 5,085,731 A | 2/1992 | Norman et al. |
| 5,098,516 A | 3/1992 | Norman et al. |
| 5,139,999 A | 8/1992 | Gordon et al. |
| 5,144,049 A | 9/1992 | Norman et al. |
| 5,204,314 A | 4/1993 | Kirlin et al. |
| 5,225,561 A | 7/1993 | Kirlin et al. |
| 5,235,078 A | 8/1993 | Pohl et al. |
| 5,280,012 A | 1/1994 | Kirlin et al. |
| 5,322,712 A | 6/1994 | Norman et al. |
| 5,362,328 A | 11/1994 | Gardiner et al. |
| 5,453,494 A | 9/1995 | Kirlin et al. |
| 5,502,128 A | 3/1996 | Flores et al. |
| 5,536,323 A | 7/1996 | Kirlin et al. |
| 5,711,816 A | 1/1998 | Kirlin et al. |
| 5,820,664 A | 10/1998 | Gardiner et al. |
| 5,834,058 A | 11/1998 | Wallbridge et al. |
| 5,919,522 A | 7/1999 | Baum et al. |
| 5,932,363 A | 8/1999 | Hu et al. |
| 6,110,529 A | 8/2000 | Gardiner et al. |
| 6,211,090 B1 | 4/2001 | Durlam et al. |
| 6,294,836 B1 | 9/2001 | Paranjpe et al. |
| 6,337,148 B1 | 1/2002 | Xu et al. |
| 6,417,369 B1 | 7/2002 | Xu et al. |
| 6,440,202 B1 | 8/2002 | Xu et al. |
| 6,444,263 B1 | 9/2002 | Paranjpe et al. |
| 6,639,080 B2 | 10/2003 | Xu et al. |
| 6,818,783 B2 | 11/2004 | Norman et al. |
| 6,969,539 B2 | 11/2005 | Gordon et al. |
| 7,557,229 B2 | 7/2009 | Gordon et al. |
| 8,299,286 B2 | 10/2012 | Gardiner et al. |
| 2002/0081381 A1 | 6/2002 | DelaRosa et al. |
| 2002/0132375 A1 | 9/2002 | Doan et al. |
| 2002/0173054 A1 | 11/2002 | Kim |
| 2004/0175502 A1 | 9/2004 | Senzaki |
| 2005/0042372 A1 | 2/2005 | Denk et al. |
| 2005/0214458 A1 | 9/2005 | Meiere |
| 2005/0281952 A1 | 12/2005 | Xu et al. |

(Continued)

FOREIGN PATENT DOCUMENTS

| | | |
|---|---|---|
| DE | 4039449 | 6/1992 |
| EP | 1 142 894 B1 | 10/2001 |

(Continued)

OTHER PUBLICATIONS

Cotton et al., Inorg. Chem., (2006), 45, pp. 5493-5500.*
STN Registry Database entry for CAS RN 78316-86-6, Published in database Nov. 16, 1984.*
Cotton et al., Inorg. Chem. 2006, 45, pp. 5493-5500.*
Mazurek et al., Inorg. Chem., (1985), 24, pp. 3258-3264.*
STN Registry database entry for CAS RN 42116-77-8, Published in STN Registry Nov. 16, 1984; Accessed Sep. 5, 2014.*
Aspinall, et al., "A Synthesis of 2-Alkylamino-4, 5-dihydroimidazoles," The Monomagnesium Derivatives of Dibromotoluenes, Feb. 1951, vol. 73, pp. 602-603.

(Continued)

*Primary Examiner* — Alicia L Otton
(74) *Attorney, Agent, or Firm* — Wilmer Cutler Pickering Hale and Dorr LLP

(57) ABSTRACT

Bicyclic guanidine compounds are described. Metal bicyclic guanidinate and its use in vapor deposition processes to deposit a metal-containing thin film are also described. Methods of making alkaline earth metal N,N'dialkylacetamidinates or bicyclic guanidinates including dissolution of alkaline earth metal into liquid ammonia followed by addition of a solution of an amidine or guanidine ligand in the free base from are provided.

21 Claims, 1 Drawing Sheet

(56) References Cited

U.S. PATENT DOCUMENTS

| | | | |
|---|---|---|---|
| 2006/0062910 A1 | 3/2006 | Meiere | |
| 2006/0140155 A1 | 6/2006 | Jang et al. | |
| 2006/0177577 A1 | 8/2006 | Thompson | |
| 2006/0193979 A1 | 8/2006 | Meiere et al. | |
| 2006/0270223 A1 | 11/2006 | Millward | |

FOREIGN PATENT DOCUMENTS

| | | |
|---|---|---|
| GB | 2295392 A | 5/1996 |
| GB | 2295393 A | 5/1996 |
| WO | WO-01/68948 A1 | 9/2001 |
| WO | WO-2004/046417 | 6/2004 |
| WO | WO-2009/105668 | 8/2009 |

OTHER PUBLICATIONS

Coles, et al., "Article: Exploration of the Suitability of Bicyclic Guanidinates as Ligands in Catalytic Chemistry Mediated by Titanium," Organometallics, Abstract, 2003, 22 (25), 1 page, retrieved from http://pubs.acs.org/doi/abs/10.1021/om0341092.

Corey et al., "Enantioselective Synthesis of α-Amino Nitriles from N-Benzhydryl Imines and HCN with a Chiral Bicyclic Guanidine as Catalyst," Organic Letters, 1999, vol. 1, No. 1, pp. 157-160.

Corey, et al., "Enantiospecific Synthesis of a Rigid, $C_2$ Symmetric, Chiral Guanidine by a New and Direct Method," Tetrahedron Letters, vol. 30, No. 39, pp. 5227-5230, 1989.

International Search Report and Written Opinion of the International Searching Authority, The United States Patent and Trademark Office, for International Application No. PCT/US2009/034708, dated Apr. 14, 2009, 5 pages.

Isobe, et al., "Modified Guanidines as Potential Chiral Superbases. 2. Preparation of 1,3-Unsubstituted and 1-Substituted 2-Iminoimidazolidine Derivatives and a Related Guanidine by the 2-Chloro-1,3-dimethylimidazolinium Chloride-Induced Cyclization of Thioureas," J. Org. Chem., 2000, 65, pp. 7774-7778.

Isobe, et al., "Modified Guanidines as Potential Chiral Superbases. 3. Preparation of 1,4,6-Triazabicyclooctene Systems and 1,4-Disubstituted 2-Iminoimidazolidines by the 2-Chloro-1,3-dimethylimidazolinium Chloride-Induced Cyclization of Guanidines with a Hydroxyethyl Substituent," J. Org. Chem., 2000, 65, pp. 7779-7785.

Jones et al., "378. Reactions of Nitroparaffins. Part II. The Reaction of 2-Nitropopane with Formaldehyde and Ammonia," Reactions of Nitroparaffins. Part II., Feb. 1949, pp. 1766-1767 (retrieved from http://pubs.rsc.org/doi:10,1039/JR9490001766 on Feb. 24, 2011).

McKay, et al., "A New Molecular Rearrangement. II. Confirmation of Structures and Extension of the Rearrangement Reaction," The Journal of the American Chemical Society, vol. LXXVIII, Oct.-Dec. 1956, pp. 6144-6147.

McKay, et al., "Amino Acids. II. Synthesis of Cyclic Guanidino Acids[1]," Sep. 23, 1955, J. Am. Chem. Soc., vol. 78, pp. 1618-1620.

McKay, et al., "Chemistry of 2,3,5,6-Tetrahydro-1-Imidaz(1,2-a) Imidazole[1]," Canadian Journal of Chemistry, vol. 35, 1957, pp. 843-849.

Osby, et al., "Rapid and Efficient Reduction of Aliphatic Nitro Compounds to Amines," Tetrahedron Letters, vol. 26, No. 52, pp. 6413-6416, 1985.

Ritala, et al, "Chapter 2: Atomic Layer Deposition," Handbook of Thin Films Materials, vol. 1, 2002, pp. 103-159, Edited by Han Singh Nalwa, Academic Press.

Thirupathi, et al., "Group 5 Transition Metal Imido Complexes with Dianionic Guanidinate Ligands Displaying Extended Interactions," Chem. Commun., 1999, pp. 2483-2484.

Barker et al., "The Coordination Chemistry of the Amidine Ligand," Coordination Chemistry Reviews, vol. 133, pp. 219-300 (No Month Listed 1994), 82 pages.

Barker, J. et al. "N,N'-Unsubstituted Amidinato Metallacycle Complexes of Group 13 Metal Alkyls: The Crystal Structure of Trimeric [Me$_2$Al(μ-HNCPhNH)}$_3$]." Journal of Organometallic Chemistry. Elsevier Sequoia S.A. Lausanne, Switzerland. vol. 596, No. 2, Sep. 5, 1999, pp. 138-144, 7 pages.

Berno et al., "Dinitrogen Fixation versus Metal-Metal Bond Formation in the Chemistry of Vanadium(II) Amidinates," J. Am. Chem. Soc., vol. 116, pp. 7417-7418 (No Month Listed 1994), 2 pages.

Coles, M.P. et al., "Synthesis and Structures of Mono- and Bis(amidinate) Complexes of Aluminum," Organometallics, vol. 16, pp. 5183-5194 (No Month Listed 2007), 12 pages.

Cotton, F. Albert et al., "Experimental and theoretical studies of the copper(I) and silver(I) dinuclear N,N'-Di-p-tolylformamidinato complexes," J. Am. Chem. Soc., vol. 110, No. 21, pp. 7077-7083 (Oct. 1988).

Edelmann, "N-silylated Benzamidines: Versatile Building Blocks in Main Group and Coordination Chemistry," Coordination Chemistry Reviews, vol. 137, pp. 403-481 (No Month Listed 1994), 78 pages.

Hao et al., "Ligand Steric Bulk: A Neglected Factor in the Formation of Cr—Cr Supershort Contacts," Inorganica Chimica Acta, vol. 213, pp. 65-74 (No Month Listed 1993), 10 pages.

Hao et al., "The role of ligand steric hindrance in determining the stability of very short V—V contacts. Preparation and characterization of a series of V(II) and V(III) amidinates," Inorganica Chimica Act, vol. 244, pp. 37-49 (No Month Listed 1996), 13 pages.

Kilner, Melvyn et al., "Studies of amidino-complexes of copper(I) and (II). Carboxylate analogues," Polyhedron, vol. 2, No. 12, pp. 1379-1388 (No Month Listed 1983), 10 pages.

Lim et al., "Synthesis and Characterization of Volatile, Thermally Stable, Reactive Transition Metal Amindates," Inogranic Chemistry, vol. 42, pp. 7951-7958 (No Month Listed 2003).

Lim, B. et al., "Atomic layer deposition of transition metals," Nature Materials, vol. 2, pp. 749-754 (Nov. 2003), published online Oct. 26, 2003, 6 pages.

Raskias Dias, H.V. et al., "Coinage Metal Complexes of 3,5-bis(trifluoromethyl)pyrazolate Ligand: Synthesis and Characterization of {[3,5-(CF$_3$)$_2$Pz]Cu}$_3$ and {[3,5-(CF$_3$)$_2$Pz]Ag}$_3$," Journal of Fluorine Chemistry, vol. 103, pp. 163-169 (No Month Listed 2000), 7 pages.

Sadique et al., "Monomeric and Dimeric Amidinate Complexes of Magnesium," Inorg. Chem., vol. 40, pp. 6349-6355 (No Month Listed 2001), 7 pages.

Schmidt, Joseph A.R. et al. :First-row Transition Metal Complexes of Sterically-hindered Amidinates. J. Chem Soc. Dalton Trans. Aug. 15, 2002. pp. 3454-3461. 8 pages.

Shibayama, K et al. "Living Polymerization of Carbodiimides Initiated by Copper(I) and Copper(II) Amidinate Complexes." MacroMolecules, American Chemical Society. Easton, US. vol. 30, No. 11. Jun. 2, 1997. pp. 3159-3163. 5 pages.

Vendemiati et al., "Paramagnetic Bis(amidinate) Iron(II) Complexes and their Diamagnetic Dicarbonyl Derivatives," Eur. J. Inorg. Chem., pp. 707-711 (No Month Listed 2001), 5 pages.

Zhengwen Li et al., "Synthesis and Characterization of Copper(I) Amidinates as Precursors for Atomic Layer Deposition (ALD) of Copper Metal," Inorganic Chemistry, vol. 44, No. 6, pp. 1728-1735 (No Month Listed 2005), 8 pages.

Cole, et al., "The Synthesis of a Sterically Hindered samarium(II) bis(amidinate) and Conversion to its Homoleptic Trivalent Congener", ChemComm, Issue 21, pp. 2695-2697, No Month Given, 2005, 3 pages.

* cited by examiner

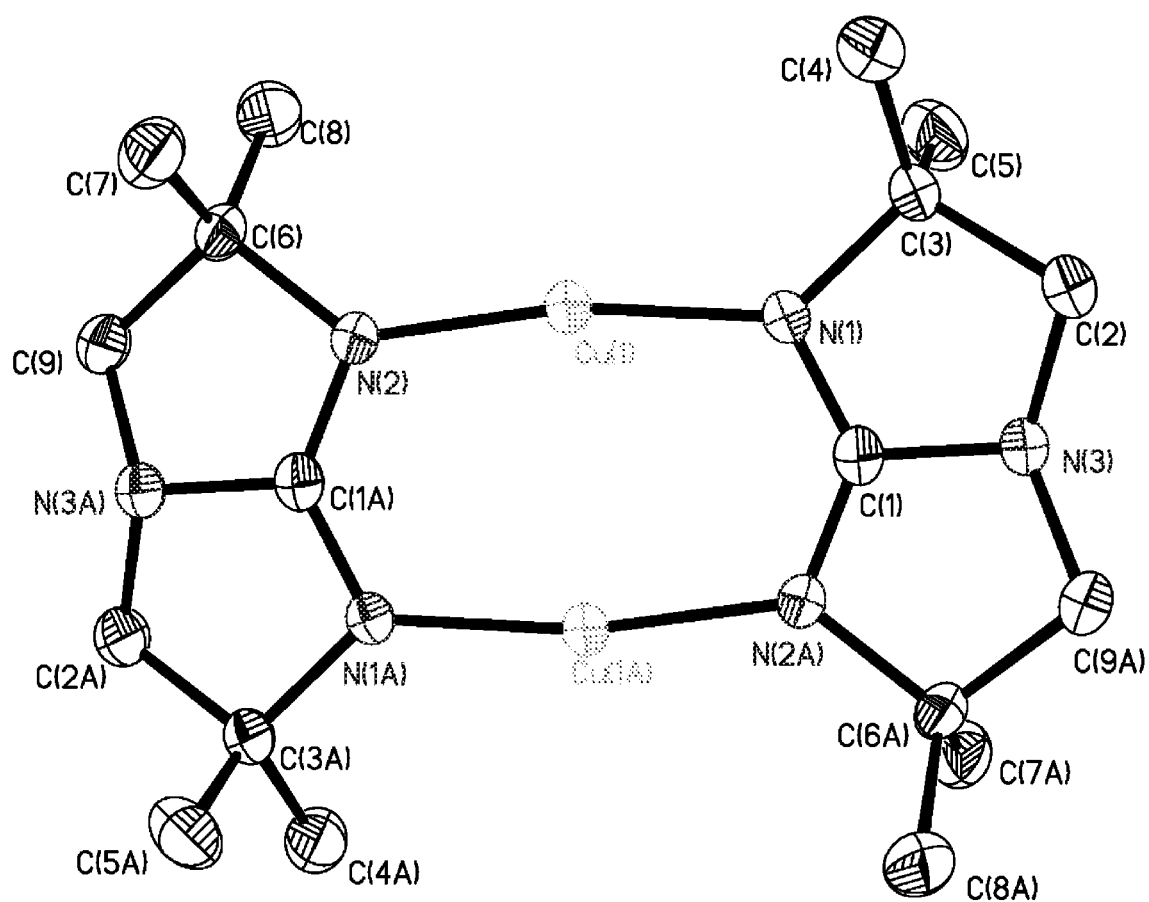

BICYCLIC GUANIDINES, METAL COMPLEXES THEREOF AND THEIR USE IN VAPOR DEPOSITION

STATEMENT REGARDING FEDERALLY SPONSORED RESEARCH

The present invention was made with United States government support under Grant No. 0354213 awarded by the National Science Foundation. The United States government has certain rights in this invention.

CROSS-REFERENCE TO RELATED APPLICATIONS

This application is related to U.S. patent application Ser. No. 10/534,687 filed on Nov. 14, 2003, entitled "Atomic layer deposition using metal amidinates," which is incorporated herein by reference in its entirety.

This application is related to U.S. Provisional Patent Application No. 60/817,209 filed on Jun. 28, 2006, entitled "Metal (IV) Tetra-Amidinate Compounds And Their Use In Vapor Deposition," which is incorporated herein by reference in its entirety.

This application claims the benefit of priority under 35 U.S.C. §119(e) to copending U.S. Application No. 61/030,063, filed Feb. 20, 2008, and entitled "Guanidines, Metal Complexes Thereof and Their Use in Vapor Deposition," which is hereby incorporated in its entirety by reference.

INCORPORATION BY REFERENCE

All patents, patent applications and publications cited herein are hereby incorporated by reference in their entirety in order to more fully describe the state of the art as known to those skilled therein as of the date of the invention described herein.

BACKGROUND

1. Field of the Invention

This invention relates to novel bicyclic guanidine compounds. This invention also relates to metal-bicyclic guanidinate compounds and the use of these compounds as precursors in vapor deposition processes.

This invention also relates to methods for producing metal amidinates.

2. Description of the Related Art

Electrically insulating materials with high dielectric constants ("high-k dielectrics") are now being used in the manufacture of computer memories (dynamic random access memories, or DRAMs). Aluminum oxide and tantalum oxide are currently in commercial use in DRAMs, and oxides, nitrides and silicates of hafnium, zirconium and lanthanum are being tested as alternatives for future use. These high-k materials may also be used as insulators in transistors in microelectronic devices.

Electrically conductive nitrides of metals such as tantalum, tungsten, hafnium, zirconium, titanium, niobium and molybdenum have a variety of applications and potential applications, such as barriers against the diffusion of copper, and as electrodes for capacitors and transistors in microelectronic devices. These refractory metals also find use as adhesion-promoting layers for copper, and as electrodes or electrical interconnections.

Vapor deposition is a preferred method for making these materials. Vapor deposition is a generic term that comprises chemical vapor deposition (CVD) and atomic layer deposition (ALD). In a CVD process, one or more vapors are delivered to a surface on which solid material is deposited; the chemical reactions that convert the vapor to a solid are initiated by means such as heat, light or electrical excitation (plasma activation). In an ALD process, two or more vapors are delivered alternately to the surface on which reactions take place to deposit a solid product. ALD is capable of depositing these materials uniformly inside the very narrow structures in modern DRAMs. CVD generally provides higher deposition rates than ALD, but with less uniform deposition inside very narrow holes.

Successful precursors for vapor deposition must be volatile, thermally stable, and highly reactive. Identifying compounds that meet all of these challenging requirements is difficult. Fully satisfactory precursors for metals such as barium, strontium, hafnium, zirconium, tantalum, niobium, tungsten, molybdenum, tin, tellurium and uranium are not known. Halides, such as $ZrCl_4$, $HfCl_4$, and $TaCl_5$, have difficulty nucleating on some substrate surfaces, and the byproduct hydrochloric acid prevents fully conformal deposition inside narrow holes. Alkoxides and dialkylamides have less than optimal thermal stabilities. Organometallic compounds may lack suitable reactivity, leaving carbon as an impurity in the films. Thus there is a need for more volatile, thermally stable, and highly reactive sources for these metals.

The deposition of strontium oxides in thin films is of interest towards the formation of electrically insulating layers with a high dielectric constant. These films, whether as a simple oxide or a component of mixed oxides such as strontium titanate or as strontium bismuth tantalite, have possible applications within the fields of microwave, semiconductor and ferroelectric, electronics and optical devices, in addition to the inclusion in multicomponent superconductors These films have been studied for the applicability of chemical vapor deposition to their creation from mixed strontium-tantalum precursors or strontium β-diketonate precursors. The conformality and thickness control of the Atomic Layer Deposition (ALD) film growth method becomes more advantageous as the complexity of electronic devices further increases while the fabrication length scales decrease.

Metal N,N'-dialkylacetamidinate precursors have been reported for CVD and ALD applications. However, the use of ALD is limited by the availability of compounds with sufficient volatility and reactivity for use as precursors. New synthetic routes providing high yields of high purity precursor materials are also desired.

SUMMARY

One aspect of the disclosure includes coordination compounds based on bicyclic guanidine compounds as ligands. In one or more embodiments, the bicyclic guanidine compounds have the general formula:

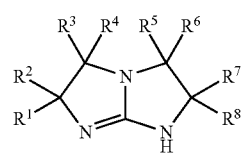

in which each of $R^1$ through $R^8$ are independently selected from the group consisting of hydrogen, hydrocarbon groups, substituted hydrocarbon groups, and other groups of non-metallic atoms. The hydrocarbon groups are preferably non-aromatic.

After deprotonation, these bicyclic guanidine compounds become anionic guanidinate ligands that may be described by three resonance forms:

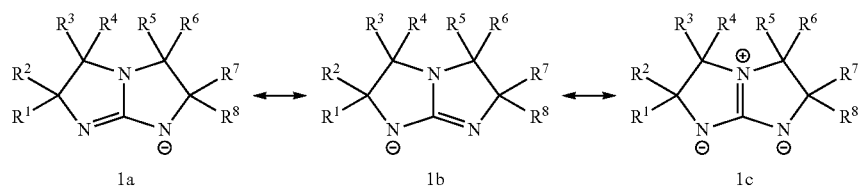

The three resonance forms can be represented by the abbreviated description below:

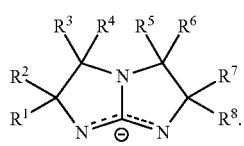

The anionic guanidinate ligand 2 is a bicyclic guanidinate ligand and can form complexes with a variety of metals. Depending on the charge of the metal, the metal can form compounds containing one, two, three or more anionic guanidinate ligands. In addition, the compound can contain neutral or other anionic ligands.

One aspect of the disclosure includes novel metal bicyclic guanidinate compounds having the general formula, $M_xG_yL_z$, where M is a metal or a semiconductor, G is a bicyclic guanidinate ligand 2, in which each of $R^1$ through $R^8$ are independently selected from the group consisting of hydrogen, hydrocarbon groups, substituted hydrocarbon groups, and other groups of non-metallic atoms, where x, y and z are selected to satisfy the charge neutrality of the compound, and L is a neutral or anionic ligand.

Examples of this aspect include compounds of formula 2a:

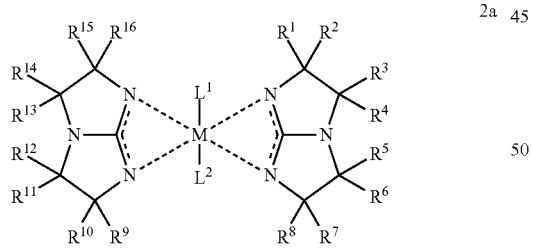

in which M is a metal or semiconductor M(II) in the +2 oxidation state and $L^1$ and $L^2$ are neutral ligands. Examples of neutral ligands are CO, alkenes, alkynes and phosphines. Other examples of this formula include a metal or semiconductor M(IV) in oxidation state +4 and $L^1$ and $L^2$ are mono-anionic ligands. Examples of mono-anionic ligands include methyl, methoxy and dimethylamido groups.

One aspect of the disclosure includes novel bicyclic guanidinate compounds containing a metal M(I) in oxidation state +1 and having the formula of type 3:

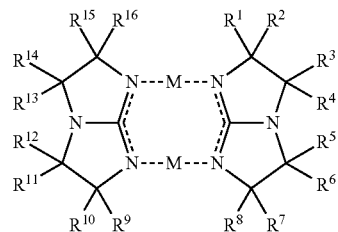

in which each of $R^1$ through $R^{16}$ are independently selected from the group consisting of hydrogen, hydrocarbon groups, substituted hydrocarbon groups, and other groups of non-metallic atoms. Also included in the compound may be neutral ligands. Some examples of neutral ligands are alkenes, alkynes or phosphines. Particularly suitable metals M(I) in oxidation state +1 include Cu(I), Ag(I), Au(I), Ir(I), In(I), Tl(I), Li(I), Na(I), K(I), Rb(I) and Cs(I). The compound may form oligomers. For example, compound 3 is shown as a dimer, e.g., $(MG)_2$. Other oligomers of the same monomeric unit, such as trimers or tetramers, are also contemplated.

Examples of this aspect include bicyclic guanidinate compounds with formulas of type 3a:

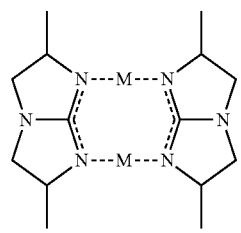

in which the metals M(I) are selected from Cu(I), Ag(I), Li(I) and Na(I), and in which $R^1$, $R^7$, $R^9$ and $R^{15}$ are methyl and the remaining R-groups are hydrogen.

Other examples of this aspect include bicyclic guanidinate compounds with formulas of type 3b:

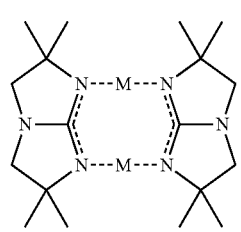

in which the metals M(I) are selected from Cu(I), Ag(I), Au(I), Ir(I), In(I) and K(I), and in which $R^1$, $R^2$, $R^7$, $R^8$, $R^9$, $R^{10}$, $R^{15}$ and $R^{16}$ are methyl and the remaining R-groups are hydrogen.

Another aspect of the disclosure includes bicyclic guanidinate compounds containing a metal or semiconductor M(II) in oxidation state +2 and having formulas of type 4:

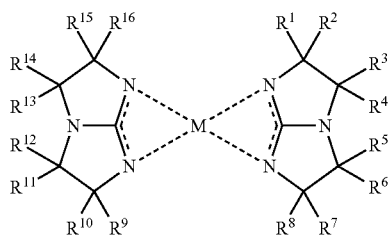

4 or oligomers thereof, in which each of $R^1$ through $R^{16}$ are independently selected from the group consisting of hydrogen, hydrocarbon groups, substituted hydrocarbon groups, and other groups of non-metallic atoms. Also included in the compound may be neutral ligands. Particularly suitable metals or semiconductors in oxidation state +2 include Be(II), Ni(II), Co(II), Cr(II), Ge(II), Zn(II), Sn(II), Mg(II), Cu(II), Fe(II), V(II), Pt(II), Mn(II), Pd(II), Ti(II), Ru(II), Ag(II), Cd(II), Ca(II), Tm(II), Hg(II), Yb(II), Dy(II), Eu(II), Sr(II), Sm(II), Pb(II), Te(II) and Ba(II).

Examples of this aspect include bicyclic guanidinate compounds with formulas of type 4a:

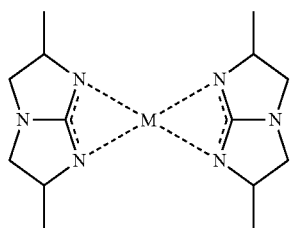

4a and its oligomers, in which the metals or semiconductors M(II) are selected from Ni(II), Co(II), Cr(II), Ge(II), Zn(II), Sn(II), Mg(II) and Fe(II), and in which $R^1$, $R^7$, $R^9$ and $R^{15}$ are methyl and the remaining R-groups are hydrogen.

Other examples of this aspect include bicyclic guanidinate compounds with formulas of type 4b:

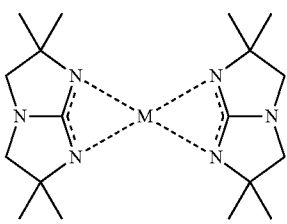

4b and its oligomers, in which the metals or semiconductors M(II) are selected from Zn(II), Sn(II), Mg(II), Cu(II), Fe(II), V(II), Pt(II), Mn(II), Pd(II), Ti(II), Ru(II), Ag(II), Cd(II), Ca(II), Tm(II), Hg(II), Yb(II), Dy(II), Eu(II), Sr(II), Sm(II), Pb(II), Te(II) and Ba(II), and in which $R^1$, $R^2$, $R^7$, $R^8$, $R^9$, $R^{10}$, $R^{15}$ and $R^{16}$ are methyl and the remaining R-groups are hydrogen.

Yet another aspect of the disclosure includes bicyclic guanidinate compounds containing a metal or semiconductor M(III) in oxidation state +3 and having the formula of type 5:

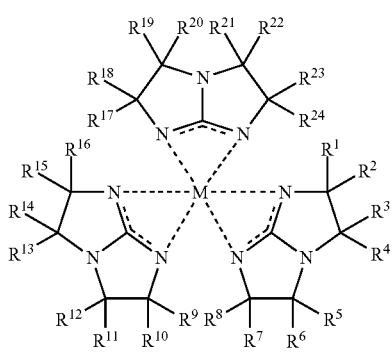

5 or oligomers thereof, in which each of $R^1$ through $R^{24}$ are independently selected from the group consisting of hydrogen, hydrocarbon groups, substituted hydrocarbon groups, and other groups of non-metallic atoms. Also included in the compound may be neutral ligands or other anionic ligands. Particularly suitable metals or semiconductors M(III) in oxidation state +3 include Al(III), As(III), Ni(III), Ga(III), Cr(III), Co(III), V(III), Fe(III), Mn(III), Ti(III), Rh(III), Ru(III), Ir(III), Mo(III), W(III), Nb(III), Ta(III), Sc(III), Sb(III), In(III), Lu(III), Yb(III), Tm(III), Er(III), Tl(III), Y(III), Ho(III), Dy(III), Tb(III), Gd(III), Eu(III), Sm(III), Nd(III), Pr(III), Ce(III), La(III) and U(III).

Examples of this aspect include compounds with formula of type 5a:

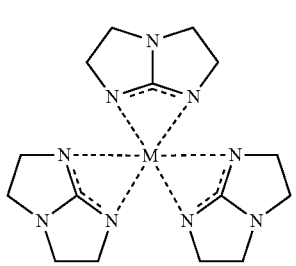

5a and its oligomers, in which the metals or semiconductors M(III) are selected from Al(III), As(III), Ni(III), Ga(III), Cr(III), Co(III), V(III), Fe(III), Mn(III), Ti(III), Rh(III), Ru(III), Ir(III), Mo(III), W(III), Nb(III), Ta(III), Sc(III), Sb(III), In(III) and Lu(III), and in which $R^1$ through $R^{24}$ are hydrogen.

Other examples of this aspect include compounds with formula of type 5b:

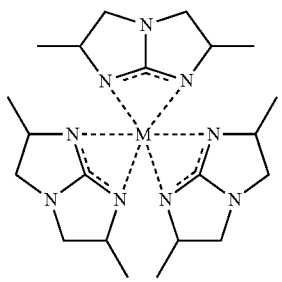

and its oligomers, in which the metals or semiconductors M(III) are selected from Sc(III), Sb(III), In(III), Lu(III), Yb(III), Tm(III), Er(III), TRIM, Y(III), Ho(III), Dy(III), Tb(III), Gd(III), Eu(III), Sm(III), Nd(III), Pr(III), Ce(III), La(III) and U(III), and in which $R^1$, $R^7$, $R^9$, $R^{15}$, $R^{17}$ and $R^{23}$ are methyl and the remaining R-groups are hydrogen.

Still another aspect of the disclosure includes bicyclic guanidinate compounds containing a metal or semiconductor M(IV) in oxidation state +4 and having the formula of type 6:

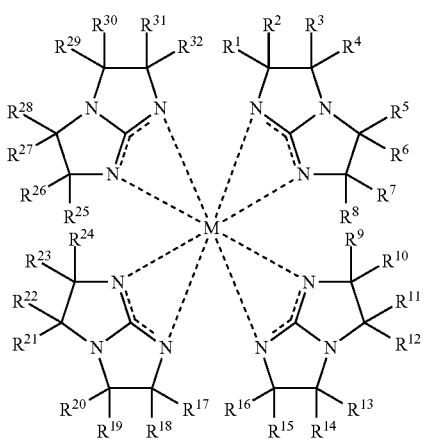

and its oligomers, in which the metals or semiconductors M(IV) are selected from Si(IV), Ge(IV), Co(IV), Fe(IV), Mn(IV), Cr(IV), V(IV), Rh(IV), Ti(IV), Ru(IV), Ir(IV), Os(IV), Re(IV), Mo(IV), W(IV), Nb(IV), Ta(IV), Sn(IV), Hf(IV), Zr(IV), Tb(IV), Pb(IV), Te(IV), Pr(IV), Ce(IV), U(IV) and Th(IV).

Examples of this aspect include bicyclic guanidinate compounds with formula of type 6a:

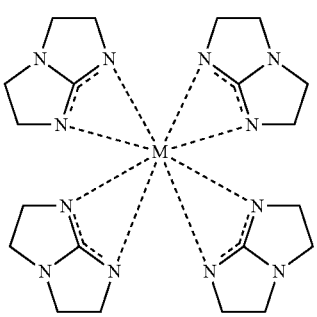

and its oligomers, in which the metals or semiconductors M(IV) are selected from Mo(IV), W(IV), Nb(IV), Ta(IV), Sn(IV), Hf(IV), Zr(IV), Tb(IV), Pb(IV) and Te(IV), and in which $R^1$ through $R^{32}$ are hydrogen.

Still another aspect of the disclosure includes use of a bicyclic guanidinate compound as a precursor in a process to deposit material from the vapor phase. This material may be in the form of films, coatings, wires, powders or other structures. Examples of the composition of the material include pure metals, metal oxides, metal nitrides, metal carbides, metal borides, metal silicides, metal sulfides, metal phosphides and combinations of these materials. Materials may also be formed by reaction or decomposition of these precursors in liquid solution, molten liquid or solid forms.

In still another aspect, methods of making alkaline earth metal N,N'-dialkylacetamidinates or bicyclic guanidinates include dissolution of alkaline earth metal into liquid ammonia followed by addition of a solution of an amidine or guanidine ligand in the free base form.

These and other aspects and embodiments of the disclosure are illustrated and described below.

BRIEF DESCRIPTION OF THE DRAWING

The aspects of the disclosure are described with reference to the figures, which are provided for the purpose of illustration only and which are not intended to be limiting of the invention.

FIG. 1 is a crystallographic x-ray structure of copper tetramethylbicycloguanidinate.

DETAILED DESCRIPTION

In one or more embodiments, a bicyclic guanidinate ligand has the structural formula:

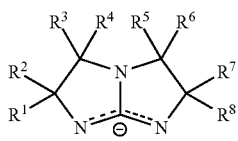

in which each of $R^1$ through $R^8$ are independently selected from the group consisting of hydrogen, hydrocarbon groups, substituted hydrocarbon groups, and other groups of nonmetallic atoms. The hydrocarbon groups are preferably non-aromatic.

Exemplary hydrocarbon groups include $C_1$-$C_6$ alkyl, $C_2$-$C_6$ alkenyl and $C_2$-$C_6$ alkynyl groups. They can be branched or unbranched.

"Alkyl group" refers to a saturated hydrocarbon chain that may be a straight chain or branched chain or a cyclic hydrocarbon group, containing the indicated number of carbon atoms. For example, $C_1$-$C_6$ indicates that the group may have from 1 to 6 (inclusive) carbon atoms in it. Examples of alkyl groups include, but are not limited to, ethyl, propyl, isopropyl, butyl, and tert-butyl groups. Examples of cyclic alkyl groups include, but are not limited to, cyclopropyl, cyclopropylmethyl, cyclobutyl, cyclopentyl, cyclohexyl, cyclohexylmethyl, cyclohexylethyl, and cycloheptyl groups.

"$C_2$-$C_6$ alkenyl group" refers to a straight or branched chain unsaturated hydrocarbon containing 2-6 carbon atoms and at least one double bond. Examples of a $C_2$-$C_6$ alkenyl group include, but are not limited to, groups derived by removing a hydrogen from ethylene, propylene, 1-butylene, 2-butylene, isobutylene, sec-butylene, 1-pentene, 2-pentene, isopentene, 1-hexene, 2-hexene, 3-hexene, and isohexene.

"$C_2$-$C_6$ alkynyl group" refers to a straight or branched chain unsaturated hydrocarbon group containing 2-6 carbon atoms and at least one triple bond. Examples of a $C_2$-$C_6$ alkynyl group include, but are not limited to, groups derived by removing a hydrogen from acetylene, propyne, 1-butyne, 2-butyne, isobutyne, sec-butyne, 1-pentyne, 2-pentyne, isopentyne, 1-hexyne, 2-hexyne, and 3-hexyne.

"Substituted hydrocarbon group" refers to a saturated or unsaturated, straight or branched chain hydrocarbon containing 1-6 carbon atoms that can be further substituted with other functional groups, such as halogen or boron, or boron-containing groups.

"Halogen" refers to an atom of fluorine, chlorine, bromine, or iodine. Halogenated hydrocarbons include fluorinated, chlorinated or brominated alkyl. Exemplary fluorinated hydrocarbons include fluoroalkyl, fluoroalkenyl and fluoroalkynyl groups and combinations thereof.

"Groups of non-metallic atoms" include nitrogen-containing and silicon-containing groups. Exemplary nitrogen-containing R groups include amines (NR'R"), in which R' and R" include one or more of H, $C_1$-$C_6$ alkyl, $C_2$-$C_6$ alkenyl or $C_2$-$C_6$ alkynyl group and combinations thereof.

Exemplary silicon-containing R groups include silyl groups (SiR'R"R'''), in which R', R" and R''' include one or more of H, $C_1$-$C_6$ alkyl, $C_2$-$C_6$ alkenyl or $C_2$-$C_6$ alkynyl group and combinations thereof.

In one or more embodiments, at least one of $R^1$ through $R^8$ is a lower alkyl group having 6 or less carbons. For compounds including more than one bicyclic guanidinate, the R-groups on the guanidinates may be similarly substituted.

In one or more embodiments, one or more of the R" are selected from the group consisting of lower alkyls having 6 or less carbons and hydrogen. For compounds including more than one bicyclic guanidinate, the R-groups on the guanidinates may be similarly substituted.

In one or more embodiments, one or more of the R" are alkyl groups that are un-branched at the α-position. For compounds including more than one bicyclic guanidinate, the R-groups on the guanidinates may be similarly substituted.

In one or more embodiments, $R^1$, $R^2$, $R^7$ and $R^8$ are methyl, and $R^3$, $R^4$, $R^5$ and $R^6$ are hydrogen. For compounds including more than one bicyclic guanidinate, the R-groups on the guanidinates may be similarly substituted.

In one or more embodiments, $R^1$ and $R^2$ are methyl, and $R^3$, $R^4$, $R^5$, $R^6$, $R^7$ and $R^8$ are hydrogen. For compounds including more than one bicyclic guanidinate, the R-groups on the guanidinates may be similarly substituted.

"Neutral ligand" refers to molecules or moieties that are neutral in charge and that are capable of forming a coordinate bond with one or more metals. Many neutral ligands are known. Exemplary neutral ligands include alkenes, alkynes, phosphines and CO.

"Anionic ligand" refers to ionic species or moieties that are negatively charged and that are capable of forming a coordinate bond with one or more metals. Many anionic ligands are known. Exemplary anionic ligands include methyl, methoxy and dimethylamido groups.

"Oligomer" refers to compounds whose molecules may be considered to contain multiple copies of a monomeric unit.

While not being bound by any particular mode or theory of operation, it is believed that the lower alkyl substituents, and in particular the unbranched lower alkyl substituents contribute to the lower melting point and increased volatility of the metal complexes with the bicyclic guanidinate ligands. Substituents that lower melting point and increase volatility, such as fluorohydrocarbons and silyl groups also promote the vapor deposition process. A lower melting point is advantageous for easy purification by distillation, convenient transfer of liquid air-sensitive compounds, and also for reproducible vaporization in a vapor deposition process. Volatility is necessary in a metal precursor compound for vapor deposition processes. The steric bulk of the substituted bicyclic guanidine ligands in a bicyclic guanidinate compound may provide steric bulk that is useful in preventing or mitigating polymerization of the compound. Polymerization would reduce the desirable volatility of the compound. Thermal stability is enhanced by the rigid structures of the bicyclic ligands and the steric bulk of their substituents, which inhibit many of the potential pathways for thermal decomposition. Oligomer size may also be limited to provide compounds with volatility and stability suitable for vapor deposition processes.

Another aspect of the disclosure includes bicyclic guanidine compounds containing a metal or semiconductor. The compound may be of the general formula, $M_xG_yL_z$, where M is a metal or semiconductor, G is a bicyclic guanidinate anion having the structure of compound 2 and L is a neutral or anionic coordinating ligand and x, y and z are selected to satisfy the charge neutrality of the compound. For example, when the metal is a monovalent metal ($M^{+1}$), x is typically 1, y is typically 1 and z can range from 0 to 3. When the metal is a divalent metal ($M^{+2}$) is typically 1, y is typically 2 and z can range from 0 to 3. The bicyclic guanidinate ligand can form multidentate and bridging complexes with the metal.

Exemplary metals include lanthanum, praseodymium and the other lanthanide metals, yttrium, scandium, titanium, vanadium, niobium, tantalum, chromium, iron, ruthenium, cobalt, rhodium, iridium, aluminum, gallium, indium, bismuth, cobalt, iron, nickel, manganese, ruthenium, zinc, titanium, vanadium, chromium, europium, magnesium, germanium, calcium, copper, silver, gold, iridium, zirconium, hafnium, tin, tantalum, niobium, tungsten, molybdenum, uranium, rhenium, platinum, osmium, iridium, ruthenium, palladium, titanium, rhodium, vanadium, cerium and lead. In specific embodiments, M is a first row transition metal such as Ni, Co, Fe, Ti, Mn or V.

Bicyclic guanidines are prepared using a variety of synthetic schemes.

In one embodiment, the guanidine moiety is formed concurrently with acid catalyzed cyclizations in which the central carbon is provided by carbon disulfide.

The exemplary compound II was prepared by a three stage route.

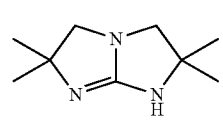

II

The initial intermediate is di-(2-nitroisobutyl)amine (III), which is then hydrogenated to di-(2-aminoisobutyl)amine (IV). This is then cyclized to form the guanidine.

The rate of ring closure was found to be influenced by temperature and by acid catalysis. The ring closures were carried out in two stages in order to achieve greater control of the reaction. The proposed reaction mechanism is presented in Scheme 1.

Scheme 1

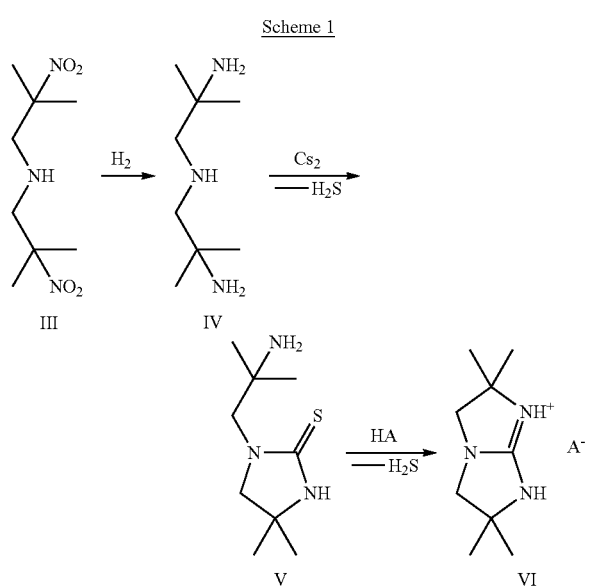

The di-(2-nitroisobutyl)amine is prepared in the manner of Kluger (Kluger, E. W.; Su, T. K.; U.S. Pat. No. 4,293,682, 1981) whereby 2-nitropropane is reacted with ammonium hydroxide and formaldehyde. An alternate route is that of Jones (Jones, J. K. N.; Urbanski, T.; *J. Chem. Soc.*, 1949, 1766), in which 2-nitropropane, sodium cyanide and formaldehyde were reacted to form compound III in lower yield. The nitro groups are reduced to amines by high pressure hydrogenation. The reaction times of the hydrogenation can be reduced by the used of elevated temperatures. It is possible to use the method of Osby (Osby, J. O.; Ganum, B.; Tetrahedron. *Lett.*, 1985, 26(52), 6413), reducing the nitro groups with NaBH$_4$ in a nickel boride solution; however the aqueous neutralization and subsequent extraction do not provide high yields. The triamine IV was found to be hydrophilic and remained preferentially in the aqueous phase during solvent extractions.

The rings were formed by reaction of the compound IV with carbon disulfide at elevated temperatures and in the presence of acid catalyst, as disclosed by A'Court (U.S. Pat. No. 4,797,487, 1989). The use of excess acid was found to reduce greatly the required reaction times and temperatures but results in the product being isolated as the di-hydrochloride salt. The preparation and isolation of compounds similar to the intermediate V have been reported (Hurwitz, M. D.; Auten, R. W.; U.S. Pat. No. 2,613,211, 1950). Separate reports describe the final ring closure of unsubstituted bicyclic guanidines through the use of inorganic sulphur traps or chloroacetic acid or the creation of monocyclic and bicyclic guanidines through the removal of sulfur with dimethylimidazolinium chloride. See, e.g., McKay, A. F.; Braun, R. O.; U.S. Pat. No. 2,816,896, 1957; McKay, A. F.; Kreling, M.-E.; Pairs, G. Y.; Braun, R. O.; Whitingham, D. J.; *Can. J. Chem.*, 1957, 35, 843; McKay, A. F.; Hatton, W. G.; *J. Am. Chem. Soc.*, 1956, 78, 1618; Isobe, T.; Fukuda, K.; Tokunaga, T.; Seki, H.; Yamaguchi, K.; Ishikawa, T.; *J. Org. Chem.*, 2000, 65(23), 7774; and Isobe, T.; Fukuda, K.; Yamaguchi, K.; Seki, H.; Tokunaga, T.; Ishikawa, T.: *J. Org. Chem.*, 2000, 65(23), 7779.

In another embodiment, the synthesis begins with a preformed ring, creates the guanidine moiety and then closes the second ring. See, McKay, A. F.; Hatton, W. G.; Braun, R. O.; *J. Am. Chem. Soc.*, 1956, 78(23), 6144. The exemplary compound XI (2,2-dimethyl-2,3,5,6-tetrahydro-1H-imidazo[1,2-a]imidazole) was prepared in a four step method set forth in Scheme 2. This second route also affords the final product as the free-base and not as an Scheme 2

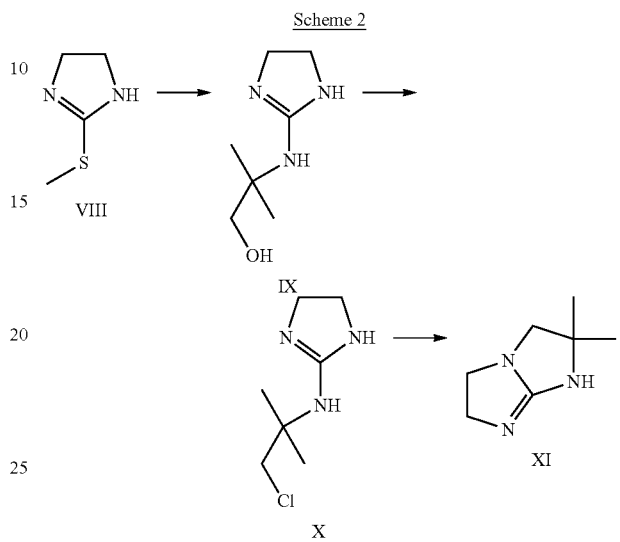

acid salt.

An alternative route provides bicyclic guanidines with singly substituted rings. See, Corey, E. J.: Ohtani, M.; *Tetrahedron Lett.*, 1989, 30(39), 5227 and Corey, E. J.; Grogan, M. J.; *Org. Lett.*, 1999, 1(1),157. This route's emphasis on maintaining chirality and the limited availability of suitable amino acids utilized as intermediates limits its applicability to the generation of a series of ligands for use in metal compounds.

The yields of the various methods are summarized in Table 1.

TABLE 1

| Product | Solvent | Time | Reactant | Yield |
|---|---|---|---|---|
| II | Toluene | 24 hours | Toluenesulphonic acid, 1 eq | impure |
| II | Toluene | 18 hours | HCl excess | 62% |
| II | MeNaphthylene | 7 days | Toluenesulphonic acid, trace | low |
| VI | MeNaphthylene | 4 Days | Toluenesulphonic acid, trace | 53% |
| XI | n-BuOH | 3 days | KOH | 59% |
| XI | n-BuOH | 3 days | Bu$_4$NOH | impure |
| XI | EtOH | 7 days | KOH | 36% |

Metal bicyclic guanidinates can be prepared by exchange reactions in which a metal dialkylamide is reacted with an amidine. Alternately, the guanidine can be converted to its alkali salt by reaction with butyllithium or with sodium amide or with potassium hydride. The alkali guanidinate can then undergo a salt metathesis reaction with a metal chloride to form the metal amidinate. Alkaline earth metals can be dissolved in liquid ammonia and then reacted with a solution of the free guanidine. The latter method has also been used to prepare alkaline earth amidinates with success.

The metal bicyclic guanidinate compounds may be used to form metal-containing films in a vapor deposition process. Vapors of the compounds according to one or more embodiments may be used to deposit materials such as metals, metal oxides, metal nitrides, metal oxynitrides, metal sulfides and the like. These vapor deposition processes include CVD and ALD. In CVD, a vapor of the metal bicyclic guanidinates is supplied to the surface, optionally along with a co-reactant gas or vapor. In ALD, a vapor of the metal bicyclic guanidinates and a co-reactant are supplied to the surface in alternating time periods. CVD processing is described, for example, in U.S. Pat. No. 5,139,999, which is hereby incorporated by reference, and in the *Handbook of Chemical Vapor Deposition: Principles, Technology and Applications* by Hugh O. Pierson (2$^{nd}$ edition, Noyes Publications, 1999). ALD processing is described in U.S. Pat. No. 6,969,539, which is hereby incorporated by reference, and in the article "Atomic Layer Deposition" by M. Ritala and M. Leskela, vol. 1, p. 103 of the *Handbook of Thin Film Materials* (Ed. H. Nalwa, Academic Press, 2002). Oxides may be formed using co-reactants such as water vapor, dioxygen, ozone, hydrogen peroxide and alcohols or a plasma formed from an oxygen-containing gas or vapor. Nitrides may be formed using co-reactants such as ammonia, a hydrazine or a plasma formed from a nitrogen-containing gas or vapor. Sulfides may be formed using co-reactants such as hydrogen sulfide or a plasma formed from a sulfur-containing gas or vapor.

In another aspect, alkaline earth metal compounds have been synthesized using alkyl derivatized acetamidines and later used to deposit strontium titanate films. By using the bis-di-tert-butylacetamidinate ligand, the described complex was found to be sufficiently volatile and reactive.

The typical method of producing acetamidinate metal complexes has been to generate the lithium salt of the amidinate from methyllithium and the corresponding carbodiimide. This is then reacted with the metal chloride yielding the desired complex and lithium chloride as a byproduct. When this route was applied to strontium chloride to produce the bis-di-tert-butylacetamidine complex, several complications arose. The first of these problems was due to the insolubility of strontium chloride in ether and THF. Ensuring the complete removal of the halide ions from the strontium, so as not to produce a heteroleptic complex with both halide and acetamidinate ligands attached, was also required. The presence of such halide ligands creates problems during film growth as they are typically liberated from the precursor during growth as the corresponding mineral acid, which then attacks both the film and any downstream equipment. The divalency of strontium combined with its large ionic radius of 1.27 Å also creates difficulties in forming monomeric, volatile complexes as the presence of just two anionic ligands may not fill the coordination sphere around the strontium ion. These problems have been resolved by preparation of strontium bis-di-tert-butylacetamidinate using the direct reaction of strontium metal with the free amidine.

While it was found that the metal was unreactive as supplied, presumably due to a passivating surface oxide, dissolution of the strontium into liquid ammonia provided a more reactive form of strontium. Into this solution, a chilled solution of the N,N'-di-tert-butylacetamidine was transferred and then the reaction mixture allowed to reach room temperature. As the ammonia boiled off, the excess strontium precipitated out of solution and only the strontium amidinate complex is left in solution. This route was found to work with other acetamidines, such as di-tert-amylacetamidine and N-dimethylethyleneamine-N'-tert-butylacetamidine, also yielding strontium complexes.

The X-ray structure of the strontium di-tert-butylacetamidinate complex shows a dimeric structure where each of the strontium atoms has one terminal ligand. The remaining two bridging ligands are bound to two different strontium atoms through the amidine nitrogens but are canted so that delocalized electrons in the ring thus formed can bond with the other strontium atom.

The thermal decomposition rate of the strontium bis-di-tert-butylacetamidinate complex was measured by the decrease in concentration of a sample in deuterated o-xylene and kept at elevated temperature. The sample was placed in a sealed glass tube maintained at 150° C. for a period of a few hours and the concentration followed by the intensity of the corresponding NMR peak. The decomposition was found to obey first order kinetics with a half-life of 141+/−24 minutes calculated at this temperature. As a result of this short half-life, the use of a liquid delivery during film growth seemed advantageous since it would store the bulk of the precursor at room temperature. The solubility of the strontium di-tert-butylacetamidinate complex was measured in several solvents that possess high boiling points, to select possible candidates for the use of this precursor in a liquid delivery system. The solubility is reported in Table 2. All of the solvents chosen provide some degree of complexation, since this offered the possibility of breaking up the dimeric structure thereby increasing the volatility. Analysis of the solutions by NMR consistently revealed a precursor structure consistent with retention of the dimeric structure.

TABLE 2

Solubility of Strontium Bis-di-tert-butylacetamidinate

| Solvent | Boiling Point (° C.) | Solubility (mole %) |
| --- | --- | --- |
| n-tributylamine | 216 | 3.0 |
| Tetramethylethylenediamine | 121 | 8.0 |
| Glyme | 84.5 | 9.4 |
| Pentamethyldiethylenetriamine | 198 | 10 |
| Hexamethyltriethylenetetramine | 130 (11 mmHg) | 20 |
| Tetraglyme | 275 | 4.1 |

The volatility of these compounds along with the observed reactivity to water makes these strontium acetamidinate complexes potential precursors for ALD. The moderate thermal instability of the bis-di-tert-butylacetamidinate precursor suggests the use of a liquid vaporization method with polyamines as the solvents of choice for depositions.

The following examples are provided for the purpose of illustration, but are not intended to be limiting of the invention.

Example 1

2,2,6,6-Tetramethyl-2,3,5,6-tetrahydro-1H-imidazo[1,2-a]imidazole (II)

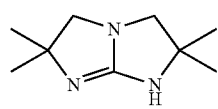

Step 1.1 Di-(2-nitroisobutyl)amine (III)

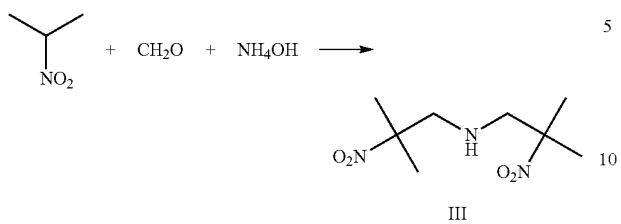

Into a 2 L flask was placed 195 mL (2.16 mol) of 2-nitropropane (97%). To this was added 300 mL (3.25 mol) of ammonium hydroxide (38%) and 450 mL of ethanol (90%). A condenser was fitted to the flask and the solution heated. Once the solution had started to reflux, 240 mL (2.96 mol) of formaldehyde (37%) was added dropwise by means of an additions funnel. Refluxing was continued for seven hours. The cooled solution was placed in an ice bath to precipitate the product. This was filtered and recrystallized from ethanol (95%). The supernatant was washed with methylene chloride to extract any remaining product, this was reduced under vacuum until all solvent had been removed. This additional crude product was recrystallized in ethanol. Total yield of purified product was 196.09 g (83%). Purity was checked by NMR, showing a singlet at 2.28 ppm and a singlet at 0.98 ppm.

Step 1.2. Di-(2-aminoisobutyl)amine (IV)

Into a 2 L pressure reactor, 21.17 g (0.0965 mol) of compound III was placed along with 600 mL of ethanol (90%). Approximately 3 g of Raney Nickel was added and the bomb was pressurized to 90 PSI with hydrogen (99.9%). The solution was stirred and intermittently repressurized with hydrogen. Over the course of 5 days, 105 PSI (0.406 mol) of hydrogen were consumed. The bomb was then depressurized and the solution filtered through celite to remove the catalyst. The filtrate was evaporated under vacuum to remove all solvent and then was vacuum distilled at room temperature and a pressure of 50 mtorr. Purified product weighed 8.031 g, giving a yield of 52%. Purity was checked by NMR, with a singlet at 2.26 ppm and a singlet at 0.96 ppm.

Step 1.3. 2,2,6,6-Tetramethyl-2,3,5,6-tetrahydro-1H-imidazo[1,2-a]imidazole (II)

A 1 L three-necked flask was fitted with a condenser, which was then vented through an empty flask into a bubbler filled with 1 M KOH. A hydrogen chloride gas generation apparatus was also connected to the reaction flask through a sparging tube. The gas generation apparatus consisted of a 100 mL three-necked flask with an additions funnel and an outlet to a drying tube filled with calcium chloride. A purified nitrogen supply was fed into the top of the additions funnel. Into the reaction flask, 3.073 g (19.3 mmol) of di-(2-aminoisobutyl) amine was placed. This was dissolved in 900 mL of toluene and stirred magnetically. The gas generation apparatus was charged with 18.8 g (322 mmol) of sodium chloride, also stirred magnetically. The system was purged with nitrogen for approximately thirty minutes. Carbon disulfide (1.5 mL, 24.8 mmol) was added to the reaction solution which caused a clouding of the solution. The solution was then stirred at room temperature for four hours and twenty minutes. Production of hydrogen chloride started after 15 mL (280 mmol) of concentrated sulfuric acid was placed in the additions funnel. This was added dropwise to the sodium chloride over the course of ten minutes. The reaction solution was then brought to reflux and heated overnight. The evolution of hydrogen sulfide was followed by the reaction of the effluent gas with lead acetate. The reaction flask was then cooled in an ice bath and filtered to remove the product. The flask was rinsed with approximately 300 mL of methylene chloride to collect any remaining product, this solution was dried and combined with the filtered product. The crude weight was 3.133 g, and this was placed in a vacuum desiccator for several days to remove adsorbed toluene. The dried weight was 2.837 g, giving a yield of 61.8%. NMR (CDCl$_3$) s 1.37 ppm, s 3.47 ppm. The acid salt was neutralized in aqueous potassium hydroxide and the water was then removed by evaporation Extraction of the residue into methyl ethyl ketone yielded the free base but often with many waters of hydration. HRMS calculated 168.1501. found 168.1499. NMR (CD$_3$OD) 2.45 (s, 4H), 1.10 (s, 12H).

Example 2

2,6-Dimethyl-2,3,5,6-tetrahydro-1H-imidazo[1,2-a]imidazole (VI)

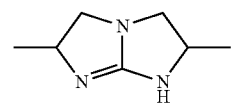

Step 2.1. Di-(2-aminopropyl)amine (VII)

Into a 500 mL flask, 180 mL of de-ionized water was placed. To this, 120 mL of 1,2-diaminopropane (1.39 mol) was added and a condenser was fitted to the flask. 50 mL (0.507 mol) of hydrogen chloride (37%) was added dropwise and the reaction allowed to subside before adding 10 mL of 2-methylaziridine (0.142 mol). The solution was then heated to 110° C. for 25 hours. The solvent and excess 1,2-diaminopropane were then removed by vacuum distillation. The crude product was then distilled under vacuum (approximately 40 torr) with a boiling point of 110° C. The yield was 24% with 4.541 g obtained. The purity was determined by NMR, showing multiplets at 2.71, 2.35 and 0.91 ppm which corresponded to those in a commercial sample. There was an additional peak at 2.11 ppm which may be due to a structural isomer of the product.

Step 2.2. 2,6-Dimethyl-2,3,5,6-tetrahydro-1H-imidazo[1,2-a]imidazole (VI)

In a 100 mL flask, 0.4078 g of di-(2-aminopropyl)amine (0.00311 mol) was dissolved in 50 mL of 1-methylnaphthalene. Carbon disulfide (0.18 mL, 0.00298 mol) was added. The reaction was stirred for three hours then heated to 200° C. The reaction was heated for four days until production of hydrogen sulfide stopped. The solvent was then removed by distillation. The product was then dissolved in approximately 5 mL of hexanes and 0.5 mL of a 2.0 M ether solution of hydrogen chloride was added. The yield of the precipitate was 0.278 g (53%). The NMR had a doublet at 1.19 ppm, a multiplet at 3.44 ppm, a multiplet at 3.92 ppm and a multiplet at 4.15 ppm.

Example 3

2,2-Dimethyl-2,3,5,6-tetrahydro-1H-imidazo[1,2-a]imidazole (XI)

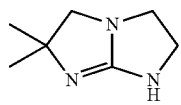

XI

Step 3.1. 2-(4,5-Dihydro-1H-imidazol-2-ylamino)-2-methyl-propan-1-ol hydroiodide (IX)

2-methylmercapto-2-imidazolinium hydroiodide was prepared from ethylene thiourea in the manner of Aspinall and Bianco (Aspinall, S. R., Bianco, E. J.; *J. Am. Chem. Soc.*, 1953, 73(2), 602). A sample of this, 62.00 g (0.254 mol) was dissolved in 250 mL of chloroform in a 500 mL round bottom flask. To this, 30 mL (28.02 g, 0.314 mol) of 2-amino-2-methylpropanol was added. A condenser was fitted to the flask and vented through a wet scrubbing column so as to capture the evolved thiomethane. The solution was refluxed for 24 hours and then purged with nitrogen to remove residual thiomethane. The solvent was removed under vacuum to yield a colourless viscous liquid. This was used directly in the subsequent reaction. NMR 3.75 (s, 2H), 3.44 (s, 2H), 2.56 (s, 1H), 2.36 (s, 1H), 1.22 (s, 6H).

Step 3.2. (2-Chloro-1,1-dimethyl-ethyl)-(4,5-dihydro-1H-imidazol-2-yl)-amine hydroiodide (X)

In a 1 L three necked round bottom flask, 48.26 g (0.169 mol) of 2-(4,5-dihydro-1H-imidazol-2-ylamino)-2-methyl-propan-1-ol hydroiodide was dissolved in 400 mL of chloroform. To this, 15 mL (24.46 g, 0.206 mol) of thionyl chloride was added dropwise at room temperature. The reaction was then refluxed for 36 hours after which the solvent was removed by vacuum. The product retained too much solvent after this to afford a yield calculation. NMR 3.56 (s, 4H), 3.35 (m, 2H), 1.28 (d, 6H).

Step 3.3. 2,2-Dimethyl-2,3,5,6-tetrahydro-1H-imidazo[1,2-a]imidazole (XI)

A solution of (2-chloro-1,1-dimethyl-ethyl)-(4,5-dihydro-1H-imidazol-2-yl)-amine hydroiodide (12.5 g, 0.0412 mol) in 100 mL of n-butanol was prepared in a 250 mL three necked flask fitted with a condenser, Dean-Stark trap and a syringe pump. The alkaline solution was prepared from 5.38 g (0.0959 mol) of potassium hydroxide in 63 mL of n-butanol. The guanidine solution was brought to reflux and the alkaline solution added over a period of three days. Negligible amounts of water were collected in the Dean-Stark trap. The greenish by-product precipitate was removed by filtration and the supernatant was concentrated by evaporation. Purification from methyl ethyl ketone and ether gave 3.41 g of product, 59.4% yield. NMR 2.55 (m, 4H), 3.25 (s, 2H), 1.20 (s, 6H).

Example 4

Calcium bis-tetramethylbicycloguanidinate 7

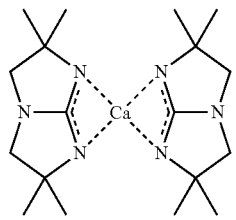

7

The tetramethylbicycloguanindine hydrochloride salt (2,2,6,6-tetramethyl-2,3,5,6-tetrahydro-1H-imidazo[1,2-a]imidazole) from Example 1 (1.078 g, 4.49 mmol) was placed in a flask with 100 mL of THF. Calcium hydride (0.65 g, 15.4 mmol) was added and the reaction was stirred overnight, at which point all the calcium hydride was consumed. The THF was removed under vacuum and the reaction product was extracted into toluene. This was filtered and then the toluene was removed under vacuum to provide the crude product with a yield of 30%. Sublimed at 60° C./30 mtorr with 51% yield. A test by the reaction of the sublimed material with acid followed treatment with alkaline ammonium oxalate solution showed the presence of calcium. NMR (C$_6$D$_6$) 0.68 (s, 6H), 0.951 (s, 6H), 3.01 (s, 2H), 3.32 (s, 2H).

Example 5

Strontium bis-tetramethylbicycloguanidinate 8

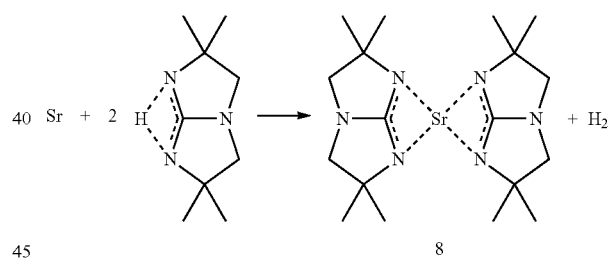

8

This compound can be prepared by reacting the tetramethylbicycloguanindine (2,2,6,6-tetramethyl-2,3,5,6-tetrahydro-1H-imidazo[1,2-a]imidazole) with strontium metal dissolved in liquid ammonia.

Example 6

Nickel bis(tetramethylbicycloguanidinate) 9

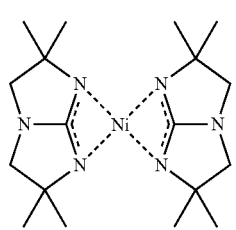

9

This compound can be prepared by reacting the tetramethylbicycloguanindine hydrochloride salt (2,2,6,6-tetramethyl-2,3,5,6-tetrahydro-1H-imidazo[1,2-a]imidazole) from Example 1 with butyllithium and then with NiCl$_2$.

Example 7

Cobalt bis(tetramethylbicycloguanidinate) 10

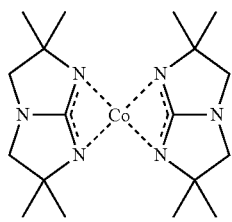

10

This compound can be prepared by reacting the tetramethylbicycloguanindine hydrochloride salt (2,2,6,6-tetramethyl-2,3,5,6-tetrahydro-1H-imidazo[1,2-a]imidazole) from Example 1 with butyllithium and then with CoCl$_2$.

Example 8

Copper tetramethylbicycloguanidinate 11

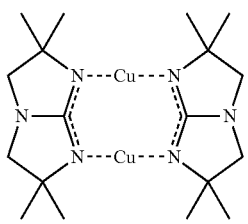

11

This compound can be prepared by reacting the tetramethylbicycloguanindine hydrochloride salt (2,2,6,6-tetramethyl-2,3,5,6-tetrahydro-1H-imidazo[1,2-a]imidazole) from Example 1 with butyllithium and then with CuCl. Its molecular structure is shown in FIG. 1. This copper tetramethylbicycloguanidinate was dissolved in deuterated mesitylene and heated to 200° C. in a sealed NMR tube for 4 days. No significant change was noted in the NMR spectrum or in the color of the solution. A control sample of copper N,N'-di-sec-butylacetamidinate showed significant decomposition and color change under the same conditions. These experiments demonstrate the superior thermal stability of this copper tetramethylbicycloguanidinate.

Example 9

Copper bicycloguanidinate 12

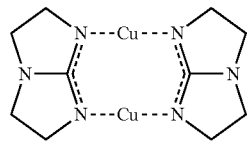

12

This compound can be prepared by reacting 2,3,5,6-tetrahydro-1H-imidazo[1,2-a]imidazole, made according to U.S. Pat. No. 4,797,487, with butyllithium and then with CuCl in THF. After the THF is evaporated, the product is extracted from the LiCl with benzene and then sublimed for purification.

Example 10

Silver tetramethylbicycloguanidinate 13

This compound can be prepared by reacting the tetramethylbicycloguanindine hydrochloride salt (2,2,6,6-tetramethyl-2,3,5,6-tetrahydro-1H-imidazo[1,2-a]imidazole) from Example 1 with butyllithium and then with AgCl.

Example 11

Ruthenium bis(dimethylbicycloguanidinate)dicarbonyl 14

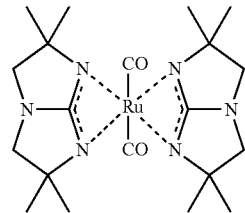

14

This compound can be prepared by reacting the tetramethylbicycloguanindine hydrochloride salt (2,2,6,6-tetramethyl-2,3,5,6-tetrahydro-1H-imidazo[1,2-a]imidazole) from Example 1 with butyllithium and then with [RuCl$_2$(CO)$_3$]$_2$.

Example 12

Titanium tris(bicycloguanidinate) 15

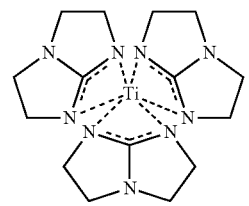

15

This compound can be prepared by reacting bicycloguanindine (2,3,5,6-tetrahydro-1H-imidazo[1,2-a]imidazole) with butyllithium and then with TiCl₃(THF)₃.

Example 13

Lanthanum tris(dimethylbicycloguanidinate) 16

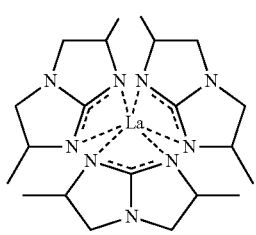

This compound can be prepared by reacting the tetramethylbicycloguanindine hydrochloride salt (2,6-dimethyl-2,3,5,6-tetrahydro-1H-imidazo[1,2-a]imidazole) from Example 2 with butyllithium and then with LaCl₃(THF)₃.

Example 14

Zirconium tetrakis(bicycloguanidinate) 17

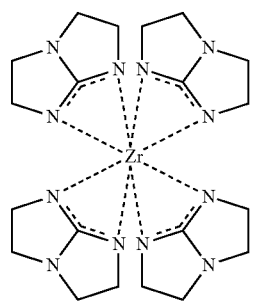

This compound can be prepared by reacting the bicycloguanindine(2,3,5,6-tetrahydro-1H-imidazo[1,2-a]imidazole with butyllithium and then with ZrCl₄.

Example 15

Dimethylzirconium bis(tetramethylbicycloguanidinate) 18

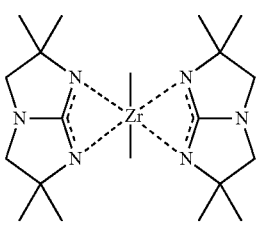

This compound can be prepared by reacting 2 equivalents of the tetramethylbicycloguanindine hydrochloride salt (2,2,6,6-tetramethyl-2,3,5,6-tetrahydro-1H-imidazo[1,2-a]imidazole) from Example 1 with butyllithium and then with ZrCl₄, followed by reaction with 2 equivalents of methyllithium.

Example 16

Strontium bis-di-tert-butylacetamidinate dimer 19

Into a 200 mL flask was placed 2.006 g of strontium metal (99%, 23 mmol) from which the packing oil had been blotted off. This was cooled in a dry ice/acetone bath under nitrogen. Ammonia was admitted into the flask until the strontium was dissolved in approximately 50 mL of liquid ammonia, yielding a dark blue solution.

The di-tert-butylacetamidine ligand (2.673 g, 15.7 mmol) was placed in a 100 mL flask and diluted with 50 mL of dry THF. The ligand solution was cooled in a dry ice/acetone bath and then was transferred by cannula into the cooled strontium solution. The reaction mixture was allowed to slowly warm to room temperature and left to stir overnight under nitrogen.

The solution was filtered to remove excess metal and the solvent removed under vacuum. Crude yield was 3.46 g with 3.35 g expected for Sr₂tBuAMD₄. NMR (C₆D₆) 2.1 (s, 3H), 2.0 (s, 3H), 1.4 (s, 6H), 1.3 (s, 6H). Solubilities were measured for tributylamine (6.6% w/w, 3.0% mol/mol), tetramethylethylenediamine (24.3% w/w, 8% mol/mol), glyme (32.5% w/w, 9.4% mol/mol), pentamethyldiethylenetriamine (21.4% w/w, 10% mol/mol), hexamethyltriethylenetetramine (32% w/w, 20% mol/mol) and tetraglyme (7.6% w/w, 4.1% mol/mol) with the molar ratios calculated on the basis of a monomer dissolved species.

Crystallization from pentane at −35° C. yielded an off-white solid with a melting point above 260° C. Thermogravimetric analysis shows an onset of sublimation at 250° C. under nitrogen with a residue of 30%. The compound is decomposed by ambient air at room temperature within five minutes.

A sample for the thermal decomposition study was prepared in deuterated o-xylene with a heavy walled NMR tube and sealed under vacuum. NMR spectra were taken at room temperature after each subsequent period of heating inside of an oven at 150° C. The integrated areas of the ligand methyl groups were normalized to the solvent peak for comparisons between spectra. At each time point, the natural logarithm of the ratio of the normalized peak areas to that of the spectrum measured before heating was computed. A linear fit of these data points yielded the half life of 141+/−24 minutes.

Example 17

Strontium bis-di-tert-amylacetamidinate dimer 20

This was prepared in the manner of strontium bis-di-tert-butylacetamidinate, from strontium metal and the di-tert-amylacetamidinate ligand. The crude yield was 15%. NMR (C₆D₆) 0.85 ppm (t, 3H), 1.11 ppm (t, 3H), 1.22 ppm (s, 6H), 1.29 ppm (s, 6H), 1.44 ppm (s, 3H), 1.60 ppm (q, 2H), 1.87 ppm (q, 2H).

Example 18

Strontium bis-N-di-methylethyleneamine-N'-tert-butylacetamidinate 21

This was prepared in the manner of strontium bis-di-tert-butylacetamidinate, from strontium metal and the N-di-methylethyleneamine-N'-tert-butylacetamidinate ligand. The crude yield was 22%. This was purified by sublimation at 185° C./45 mtorr with a yield of 40% %. NMR ($C_6D_6$) 1.38 ppm (m, 9H), 1.94 ppm (s, 3H), 2.26 ppm (m, 6H), 2.4 ppm (b, 2H), 3.4 ppm (b, 2H). The extra splitting of the t-butyl group and the N-methyl groups is assigned to the in equivalence of the ligands within the complex.

Example 19

Barium bis-di-tert-butylacetamidinate dimer 22

Prepared in the manner of strontium bis-di-tert-butylacetamidinate, from barium metal and the di-tert-butylacetamidinate ligand. The crude yield was 40%. Sublimed at 180° C./30 mtorr with 62% yield. NMR($C_6D_6$) 2.05 ppm (s, 3H), 1.96 ppm (s, 3H), 1.37 ppm (s, 36H).

Example 20

Calcium bis-di-tert-butylacetamidinate dimer 23

This was prepared in the manner of strontium bis-di-tert-butylacetamidinate, from calcium metal and the di-tert-butylacetamidinate ligand. The crude yield was 30%. NMR ($C_6D_6$) 1.33 ppm (s, 18H), 1.44 ppm (s, 18H), 2.01 ppm (s, 3H), 2.06 ppm (s, 3H).

It will be appreciated that while a particular sequence of steps has been shown and described for purposes of explanation, the sequence may be varied in certain respects, or the steps may be combined, while still obtaining the desired configuration. Additionally, modifications to the disclosed embodiment and the invention as claimed are possible and within the scope of this disclosed invention.

What is claimed is:

1. A bicyclic guanidinate compound having the formula, $M_xG_yL_z$, where

M is a metal or a semiconductor,

G is a bicyclic guanidinate anion having the structure

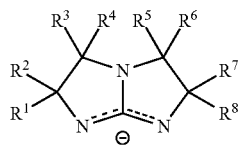

in which each of $R^1$ through $R^8$ are independently selected from the group consisting of hydrogen, hydrocarbon groups, substituted hydrocarbon groups, and other groups of nonmetallic atoms and at least one of the $R^1$ through $R^8$ is not hydrogen, and L is a neutral or anionic ligand, where x has a value of 1 or 2, with the proviso x is 1 when M is Mo(IV) in the +4 oxidation state, where y and z are selected to satisfy the charge neutrality of the bicyclic guanidinate compound.

2. A compound as in claim 1, wherein at least one of $R^1$, $R^2$, $R^7$, and $R^8$ is not hydrogen.

3. A compound as in claim 1, where the bicyclic guanidinate anion has the structure

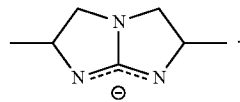

4. A compound as in claim 3, wherein x is 1, y is 3, and M is La.

5. A compound as in claim 1, where the bicyclic guanidinate anion has the structure

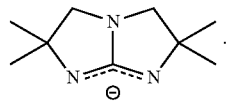

6. A compound as in claim 5, wherein x is 1, y is 2, and M is Ca, Sr, Ni, Co, or Ru.

7. A compound as in claim 6, wherein M is Ru, z is 2 and L is CO.

8. A compound as in claim 5, wherein x is 2, y is 2, and M is Cu.

9. A compound as in claim 5, wherein x is 1, y is 4, and M is Zr.

10. A compound as in claim 9, wherein z is 2 and L is methyl.

11. A compound as in claim 1, where the bicyclic guanidinate anion has the structure

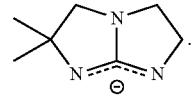

12. The compound as in claim 1, wherein M is Cu(I), Ag(I), Au(I), Ir(I), In(I), Tl(I), Li(I), Na(I), K(I), Rb(I), Cs(I), Be(II), Ni(II), Co(II), Cr(II), Ge(II), Zn(II), Sn(II), Mg(II), Cu(II), Fe(II), V(II), Pt(II), Mn(II), Pd(II), Ti(II), Ru(II), Ag(II), Cd(II), Ca(II), Tm(II), Hg(II), Yb(II), Dy(II), Eu(II), Sr(II), Sm(II), Pb(II), Te(II), Ba(II), Al(III), As(III), Ni(III), Ga(III), Cr(III), Co(III), V(III), Fe(III), Mn(III), Ti(III), Rh(III), Ru(III), Ir(III), Mo(III), W(III), Nb(III), Ta(III), Sc(III), Sb(III), In(III), Lu(III), Yb(III), Tm(III), Er(III), TRIM, Y(III), Ho(III), Dy(III), Tb(III), Gd(III), Eu(III), Sm(III), Nd(III), Pr(III), Ce(III), La(III), U(III), Si(IV), Ge(IV), Co(IV), Fe(IV), Mn(IV), Cr(IV), V(IV), Rh(IV), Ti(IV), Ru(IV), Ir(IV), Os(IV), Re(IV), Mo(IV), W(IV), Nb(IV), Ta(IV), Sn(IV), Hf(IV), Zr(IV), Tb(IV), Pb(IV), Te(IV), Pr(IV), Ce(IV), U(IV), or Th(IV), and wherein M(I) is in the +1 oxidation state, M(II) is in the +2 oxidation state, M(III) is in the +3 oxidation state and M(IV) is in the +4 oxidation state.

13. A bicyclic guanidinate compound having the formula, $M_xG_yL_z$, where

M is a metal or a semiconductor,

G is a bicyclic guanidinate anion having the structure

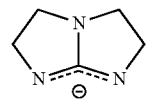

where x has a value of 1 or 2, where y and z are selected to satisfy the charge neutrality of the compound, and L is a neutral or anionic ligand, provided that M is not Mo or Au.

14. A compound as in claim 13, wherein x is 2, y is 2, and M is Cu.

15. A compound as in claim 13, wherein x is 1, y is 3, and M is Ti.

16. A compound as in claim 13, wherein x is 1, y is 4, and M is Zr.

17. A compound as in claim 16, wherein z is 2 and L is methyl.

18. A bicyclic guanidine compound having the structure

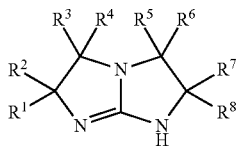

in which each of $R^1$ through $R^8$ are independently selected from the group consisting of non-aromatic hydrocarbon groups and substituted non-aromatic hydrocarbon groups.

19. A process for forming a thin film comprising a metal, comprising:

exposing a heated surface to the vapor of one or more volatile metal or semiconductor bicyclic guanidinate compounds of the formula, $M_xG_yL_z$, where M is a metal or a semiconductor, G is a bicyclic guanidinate anion having the structure

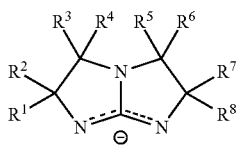

in which each of $R^1$ through $R^8$ are independently selected from the group consisting of hydrogen, hydrocarbon groups, substituted hydrocarbon groups, and other groups of nonmetallic atoms and at least one of $R^1$ through $R^8$ is not hydrogen, and L is a neutral or anionic ligand, where x has a value of 1 or 2, with the proviso x is 1 when M is Mo(IV) in the +4 oxidation state, where y and z are selected to satisfy the charge neutrality of the bicyclic guanidinate compound.

20. The process as in claim 18, wherein M is Cu(I), Ag(I), Au(I), Ir(I), In(I), Tl(I), Na(I), K(I), Rb(I), Cs(I), Be(II), Ni(II), Co(II), Cr(II), Ge(II), Zn(II), Sn(II), Mg(II), Cu(II), Fe(II), V(II), Pt(II), Mn(II), Pd(II), Ti(II), Ru(II), Ag(II), Cd(II), Ca(II), Tm(II), Hg(II), Yb(II), Dy(II), Eu(II), Sr(II), Sm(II), Pb(II), Te(II), Ba(II), Al(III), As(III), Ni(III), Ga(III), Cr(III), Co(III), V(III), Fe(III), Mn(III), Ti(III), Rh(III), Ru(III), Ir(III), Mo(III), W(III), Nb(III), Ta(III), Sc(III), Sb(III), In(III), Lu(III), Yb(III), Tm(III), Er(III), TOR), Y(III), Ho(III), Dy(III), Tb(III), Gd(III), Eu(III), Sm(III), Nd(III), Pr(III), Ce(III), La(III), U(III), Si(IV), Ge(IV), Co(IV), Fe(IV), Mn(IV), Cr(IV), V(IV), Rh(IV), Ti(IV), Ru(IV), Ir(IV), Os(IV), Re(IV), Mo(IV), W(IV), Nb(IV), Ta(IV), Sn(IV), Hf(IV), Zr(IV), Tb(IV), Pb(IV), Te(IV), Pr(IV), Ce(IV), U(IV), or Th(IV), and wherein M(I) is in the +1 oxidation state, M(II) is in the +2 oxidation state, M(III) is in the +3 oxidation state and M(IV) is in the +4 oxidation state.

21. A process for forming a thin film comprising a metal, comprising:

exposing a heated surface to the vapor of one or more volatile metal or semiconductor bicyclic guanidinate compounds of the formula, $M_xG_yL_z$, where M is a metal or a semiconductor, provided that M is not Mo or Au, G is a bicyclic guanidinate anion having the structure

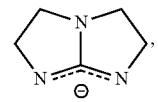

and

L is a neutral or anionic ligand, where x has a value of 1 or 2, where y and z are selected to satisfy the charge neutrality of the compound.